United States Patent
Cottens et al.

(10) Patent No.: US 6,274,629 B1
(45) Date of Patent: Aug. 14, 2001

(54) USE FOR 1,3-PROPANEDIOL DERIVATIVES

(75) Inventors: Sylvain Cottens, Witterswil; Robert Paul Hof, Gelterkinden; Roland Wenger, Riehen, all of (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/308,098

(22) PCT Filed: Nov. 17, 1997

(86) PCT No.: PCT/EP97/06408

§ 371 Date: May 17, 1999

§ 102(e) Date: May 17, 1999

(87) PCT Pub. No.: WO98/22100

PCT Pub. Date: May 28, 1998

(30) Foreign Application Priority Data

Nov. 19, 1996 (GB) .................................. 9624038

(51) Int. Cl.[7] .......................... A61K 31/135; A61K 31/04
(52) U.S. Cl. ............................... 514/646; 514/741
(58) Field of Search ..................... 514/741, 646

(56) References Cited

FOREIGN PATENT DOCUMENTS 627 406    12/1994   (EP) .
812 588    12/1997   (EP) .

OTHER PUBLICATIONS

Y.Hoshino et al., Transplantation Proceedings, "FTY720, A Novel Immunosuppressant Possessing Unique Mechanisms. II.", vol. 28, No. 2, pp. 1060–1061 (1996).

S.Suzuki et al., Transplant Immunology, "Immuynosuppressive effect of a New Drug, FTY720, on Lymphocyte Responses in Vitro and Cardiac Allograft Survival in Rats", vol. 4, No. 3, pp. 252–255 (1996).

S.Suzuki et al., Transplantation Proceedings, "Long Term Graft Acceptance in Allografted Rats and Dogs by Treatment with a Novel Immunosuppressant FTY720", vol. 28, No. 3, pp. 1375–1376 (1996).

S.Suzuki et al., Transplantation, "A Novel Immunosuppressant, FTY720, with a Unique Mechanism of Action, Induces Long–Term Graft Acceptance in Rat and Dog Allotransplantation", vol. 61, No. 2, pp. 200–205 (1996).

K.Chiba et al., Transplantation Proceedings, "FTYY720, A Novel Immunosuppressant Possessing Unique Mechanisms", vol. 28, No. 2, pp. 1056–1059 (1996).

T.Kawaguchi et al., Transplantation Proceedings, "FTY720, A Novel Immunosuppressant Possessing Unique Mechanisms III." vol. 28, No. 2, pp. 1062–1063 (1996).

Y.Hoshino et al., 9th International Congress of Immunology, "FTY720, A Novel Immunosuppressant, Possessing Unique Mechanisms. II", p. 864 (1995).

K.Adachi et al. Bioorganic & Medicinal Chemistry Letters, "Design, Synthesis, and Structure–Activity Relationship of 2–Substituted–2–Amino–1,3–Propanediols: Discovery of a Novel Immunosuppressant, FTY720", vol. 5, No. 8, pp. 853–856 (1995).

Primary Examiner—Theodore J. Criares
Assistant Examiner—Jennifer Kim
(74) Attorney, Agent, or Firm—Diane E. Furman

(57) ABSTRACT

Use of a compound of formula (I) wherein $R_1$ is an optionally substituted straight- or branched carbon chain having 12 to 22 carbon atoms which may be optionally interrupted by an optionally substituted phenylene, and each of $R_2$, $R_3$, $R_4$ and $R_5$, independently, is H or lower alkyl, in free form or in pharmaceutically acceptable salt form, in the prevention or treatment of chronic rejection in a recipient of organ or tissue allo- or xenotransplant, or of acute rejection in a xenograft transplant recipient.

(I)

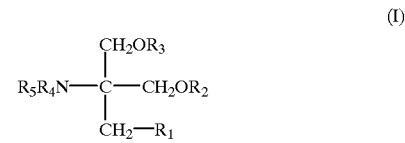

23 Claims, No Drawings

USE FOR 1,3-PROPANEDIOL DERIVATIVES

The present invention relates to a new use for a compound group comprising 2-amino-1,3-propanediol derivatives.

Compounds for use according to the invention are compounds of formula I

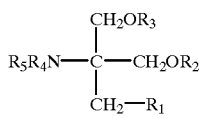

wherein
  $R_1$ is an optionally substituted straight- or branched carbon chain having 12 to 22 carbon atoms which may be optionally interrupted by an optionally substituted phenylene, and
  each of $R_2$, $R_3$, $R_4$ and $R_5$, independently, is H or lower alky,
in free form or in pharmaceutically acceptable salt form.

When the carbon chain as $R_1$ is substituted, it is preferably substituted by halogen, nitro, amino, hydroxy or carboxy. When the carbon chain is interrupted by an optionally substituted phenylene, the carbon chain is preferably unsubstituted. When the phenylene moiety is substituted, it is preferably substituted by halogen, nitro, amino, methoxy, hydroxy or carboxy.

Such compounds are disclosed in EP-A1-627,406 the relevant disclosure of which, in particular with respect to the compounds, is incorporated herein by reference.

Preferred compounds of formula I are those wherein $R_1$ is a straight or branched, preferably straight, chain alkyl having 13 to 20 carbon atoms, optionally substituted by nitro, halogen, amino, hydroxy or carboxy, and, more preferably those wherein $R_1$ is phenylalkyl substituted by a straight or branched $C_{6-14}$ alkyl chain optionally substituted by halogen and the alkyl moiety is a $C_{1-6}$ alkyl optionally substituted by hydroxy. More preferably, $R_1$ is phenyl-$C_{1-6}$ alkyl substituted on the phenyl by a straight or branched, preferably straight, $C_{6-14}$ alkyl chain. The $C_{6-14}$ alkyl chain may be in ortho, meta or para, preferably in para.

Preferably each of $R_2$ to $R_5$ is H.

Examples of the pharmaceutically acceptable salts of the compounds of the formula (I) include salts with inorganic acids, such as hydrochloride, hydrobromide and sulfate, salts with organic acids, such as acetate, fumarate, maleate, benzoate, citrate, malate, methanesulfonate and benzenesulfonate salts, and when a carboxy group is present, salts with metals such as sodium, potassium, calcium and aluminium, salts with amines, such as triethylamine and salts with dibasic amino acids, such as lysine. The compounds and salts of the present invention encompass hydrate and solvate forms.

When the compounds of formula I have one or more asymmetric centers in the molecule, the present invention is to be understood as embracing the various optical isomers, as well as racemates, diastereoisomers and mixtures thereof are embraced.

Particularly preferred compounds of formula I are 2-amino-2-tetradecyl-1,3-propanediol and especially 2-amino-2-[2-(4-octylphenyl)ethyl]-1,3-propanediol, (hereinafter Compound A) e.g. in hydrochloride form.

Compounds of formula I have, on the basis of observed activity, e.g. as described in EP-A1-627,406 been found to be useful e.g. as immunosuppressant, e.g. in the treatment of acute allograft rejection.

Organ transplants of liver, kidney, lung and heart are now regularly performed as treatment for endstage organ disease. Allograft as well as xenograft transplants have been performed. However, because of problems with long-term chronic rejection, organ transplantation is not yet a permanent solution to irreversible organ disease. Chronic rejection, which manifests as progressive and irreversible graft dysfunction, is the leading cause of organ transplant loss, in some cases already after the first postoperative year. The clinical problem of chronic rejection is clear from transplantation survival times; about half of kidney allografts are lost within 5 years after transplantation, and a similar value is observed in patients with a heart allograft.

Chronic rejection is considered as a multifactorial process in which not only the immune reaction towards the graft but also the response of the blood vessel wall in the grafted organ to injury ("response-to-injury" reaction) plays a role. The variant of chronic rejection with the worst prognosis is an arteriosclerosis-like alteration, also called transplant vasculopathy graft vessel disease, graft atherosclerosis, transplant coronary disease, etc. This vascular lesion is characterized by migration and proliferation of smooth muscle cells under influence of growth factors, that are amongst others synthesized by endothelium. It appears to progress also through repetitive endothelial injury induced amongst others by host antibody or antigen-antibody complexes, through intimal proliferation and thickening, smooth muscle cell hypertrophy repair, and finally to gradual luminal obliteration. Also so-called non-immunological factors like hypertension, hyperlipidemia, hypercholesterolemia etc. play a role.

Chronic rejection appears to be inexorable and uncontrollable because there is no known effective treatment or prevention modality. Thus, there continues to exist a need for a treatment effective in preventing, controlling or reversing manifestations of chronic graft vessel diseases.

In accordance with the present invention, it has now surprisingly been found that compounds of formula I in free form or in pharmaceutically acceptable salt form inhibit graft vessel disease and are particularly indicated to prevent or treat chronic rejection in a transplanted organ.

Furthermore, it has also been found that compounds of formula I in free form or in pharmaceutically acceptable salt form suppress xenograft rejection. In accordance with the particular findings of the present invention, there is provided:

1.1. A method of preventing or treating manifestations of chronic rejection, e.g. to avoid, reduce or restrict chronic rejection, in a recipient of organ or tissue allo- or xeno-transplant, e.g. heart, lung, combined heart-lung, liver, kidney or pancreatic transplant, comprising the step of administering to said recipient a therapeutically effective amount of a compound of formula I in free form or in pharmaceutically acceptable salt form;

1.2. A method of preventing or treating graft vessel diseases, e.g. transplant vasculopathy, arteriosclerosis or atherosclerosis, in a recipient of organ or tissue allo- or xeno-transplant, e.g. heart, lung, combined heart-lung, liver, kidney or pancreatic transplants, comprising the step of administering to said recipient a therapeutically effective amount of a compound of formula I in free form or in pharmaceutically acceptable salt form;

In a series of further specific or alternative embodiments, the present invention also provides:

2. A method of preventing or controlling acute rejection in a xenograft transplant recipient, e.g. a patient receiving a heart, lung, combined heart-lung, kidney, liver, bone marrow, pancreatic bowel, skin or corneal xenotransplant, comprising administering to said recipient a therapeutically effective amount of a compound of formula I in free form or in pharmaceutically acceptable salt form.

As alternative to the above the present invention also provides:

3. A compound of formula I in free form or in pharmaceutically acceptable salt form for use in any method as defined under 1 or 2 above; or
4. A compound of formula I in free form or in pharmaceutically acceptable salt form for use in the preparation of a pharmaceutical composition for use in any method as defined under 1 or 2 above; or
5. A pharmaceutical composition for use in any method as defined under 1 or 2 above comprising a compound of formula I in free form or in pharmaceutically acceptable salt form together with one or more pharmaceutically acceptable diluents or carriers therefor.

Utility of the compounds of formula I in free form or in pharmaceutically acceptable salt form in chronic rejection, as well as utility in treating diseases and conditions as hereinabove specified, may be demonstrated in animal tests for example in accordance with the methods hereinafter described, as well as in clinic where e.g. the transplanted organ or tissue may be submitted to regular biopsy controls and in the case of heart transplant additionally to ultrasound scanning.

A. Prevention of Graft Vessel Disease

Experimental animals:

Inbred rat strains DA ($RT1^a$, donors) and Lewis ($RT1^1$, recipients of allografts), weighing between 200 and 350 grams are used. The animals are allowed unrestricted access to food and water before and after the operation.

Carotid artery transplantation:

The rats are anaesthetised with isofluorane (Abbott), (4–5% for induction, 1.5–2% for maintenance) and 300 μg atropin sulphate is injected subcutaneously following the induction. The left carotid artery is dissected free. The artery is clamped proximally and distally and a segment of about 7–10 mm is removed. The gap is bridged by an allograft which had also been subjected to 45 min cold ischemia. Ethilon 10/o sutures are used. Finally the skin is closed with 4/0 sutures. If needed, an Alzet osmotic minipump (Alza Corp. Palo Alto, Calif.) is then implanted subcutaneously over the back (alternatively the animals are treated orally).

The rats are subject to one of the following treatments: A compound of formula I alone at the doses of 0.1 to 10 mg/kg, or in combination with Cyclosporin A at the dose of 0.03, 0.3, or 1 $mg \cdot kg^{-1} \cdot day^{-1}$ is administered for 8 weeks either by using Alzet osmotic minipumps implanted subcutaneously or alternatively by oral administration.

At 8 weeks the rats are sacrificed, the carotid arteries are perfused for 1 min with 0.1 M phosphate buffered saline solution (PBS, pH 7.4) and then for 15 min with 2.5% glutaraldehyde in phosphate buffer (pH 7.4). The carotid arteries are then excised and stained in Giemsa solution for histological evaluation.

Morphometric analysis includes the measurement of the thickness of the media and intima. A qualitative analysis of the morphological changes includes a scoring on an 0–3 scale for adventitial infiltration of mononuclear cells and necrosis (vacuolar degeneration, hypertrophy of cells), the number of smooth muscle cells (SMC) nuclei in the media (0–10, <100, >100 and >>100 nuclei for scores, 0, 1, 2 and 3 respectively, SMC necrosis (vacuolar degeneration and hypertrophy of SMC) and the intimal infiltration of mononuclear cells (13).

In both experiments, the compounds of formula 1, particularly Compound A in hydrochloride form, significantly inhibit graft infiltration and neointima formation.

B. In vivo heart xenotransplantation (hamster-to-rat)

The hamster-into-rat xenograft combination is a so-called difficult concordant combination. Rats do not have natural anti-hamster antibody in sufficient amounts to yield immediate hyperacute rejection as observed in concordant combinations; however, rejection in untreated recipients occurs within 3–4 days, by antibodies in combination with complement. This is visualized in histology by destruction of blood vessels, exsudation and extravasation of erythrocytes, and influx by polymorphonuclear granulocytes; often there are signs of hemorrhage and thrombosis. Once this rejection has been overcome by effective inhibition of antibody synthesis or complement inactivation, a cellular rejection can emerge later on. This is visualized in histology by influx of mononuclear cells, including lymphocytes, lymphoblastoid cells, and macro-phages, and destruction of the myocyte parenchyma. The inhibition of cellular rejection requires more immunosuppression than that of allografts. Congenitally athymic (rnu/rnu) rats lack a competent (thymus-dependent) cellular immune system and generally are unable to reject allografts. Such animals do reject a hamster xenograft within 3–4 days in a similar fashion as euthymic rats, indicative that (at least part of) anti-hamster antibody synthesis in rats occurs following a thymus-independent B-cell response. Such recipients are useful in hamster xenografting to evaluate rejection by thymus-independent antibody-mediated rejection.

The heart of a Syrian hamster is heterotopically transplanted in the abdomen of a male Lewis ($RT1^1$) rat with anastomoses between the donor and recipient's aorta and the donor right pulmonary artery to the recipient's inferior vena cava. The graft is monitored daily by palpation of the abdomen. Rejection is concluded in case of cessation of heart beat. Animals are weighed weekly. In the present series of experiments, the end-point is set to 28 days. Animals are subjected to autopsy; apart from the graft, weight and histology is assessed for thymus, spleen, liver, seminal vesicles and testes. Blood is taken and processed to serum for the determination of cytolytic anti-hamster erythrocyte antibody and hemolytic complement activity.

Compounds are dissolved in water and administered daily orally in a volume of 2 ml/kg body weight. Administration of 5–30 mg/kg/day, of a compound of Formula I, e.g.

Compound A in hydrochloride form, results in prolonged graft survival, in both athymic and euthymic recipients.

Daily dosages required in practicing the method of the present invention will vary depending upon, for example, the compound of formula I employed, the host, the mode of administration, the severity of the condition to be treated, and the optionally concomitantly used immunosuppressive drug e.g. CysA. A preferred daily dosage range is about from 0.03 to 2.5 mg/kg per day, particularly 0.1 to 2.5 mg/kg per day, e.g. 0.5 to 2.5 mg/kg per day as a single dose or in divided doses. Suitable daily dosages for patients are on the order of from e.g. 1 to 100 mg p.o. Suitable unit dosage forms for oral administration comprise from ca. 1 to 50 mg, usually 5 to 30 mg active ingredient, e.g. Compound A, e.g. in hydrochloride form, together with one or more pharmaceutically acceptable diluents or carriers therefor. As an alternative, the compound of formula I in free form or in pharmaceutically acceptable salt form may also be administered twice or three times a week, e.g. at a dosage as indicated above.

The compounds of formula I may be administered by any conventional route, in particular enterally, e.g. orally, for example in the form of solutions for drinking, tablets or capsules or parenterally, for example in the form of injectable solutions or suspensions. Pharmaceutical compositions comprising the compounds of formula I may be manufactured in conventional manner, e.g. as described in EP-A1-627,406.

The compounds of formula I may be administered as the sole active ingredient or together with other drugs in immunomodulating regimens or other anti-inflammatory agents. For example, the compounds of formula I may be used in combination with cyclosporins, rapamycins or ascomycins, or their immunosuppressive analogs, e.g. cyclosporin A, cyclosporin G, FK-506, rapamycin, 40-O-(2-hydroxy)ethyl-rapamycin, etc.; corticosteroids; cyclophosphamide; azathioprene; methotrexate; brequinar; leflunomide; mizoribine; mycophenolic acid; mycophenolate mofetil; 15-deoxyspergualine; immuno-suppressive monoclonal antibodies, e.g., monoclonal antibodies to leukocyte receptors, e.g., to MHC, CD2, CD3, CD4, CD7, CD25, CD28, B7, CD40, CD45, or CD58 or to their ligands; or other immunomodulatory compounds, e.g. CTLA4-lg.

Where the compounds of formula I are administered in conjunction with other immunosuppressive/immunomodulatory therapy, e.g. for preventing or treating chronic rejection as hereinabove specified, dosages of the co-administered immunosuppressant or immunomodulatory compound will of course vary depending on the type of co-drug employed, e.g. whether it is a steroid or a cyclosporin, on the specific drug employed, on the condition being treated, and so forth. In accordance with the foregoing the present invention provides in a yet further aspect:

6. A method as defined above comprising co-administration, e.g. concomitantly or in sequence, of a therapeutically effective amount of a compound of formula I and a second drug substance, said second drug substance being an immunosuppressant or immunomodulatory drug, e.g. as set forth above.
7. A Wit or package for use in any method as defined under 1 or 2 above, comprising a compound of formula 1, in free form or in pharmaceutically acceptable salt form, with at least one pharmaceutical composition comprising an immunosuppressant or immunomodulatory drug. The kit or package may comprise instructions for its administration.

| Formulation Example: soft capsules | |
|---|---|
| Compound of formula I, e.g. Compound A | 30 mg |
| Polyethylene glycol 300 | 300 mg |
| Polysorbate 80 | 20 mg |
| Total | 350 mg |

Compounds of formula I in free form or in pharmaceutically acceptable salt form are well tolerated at dosages required for use in accordance with the present invention. For example, the acute $LD_{50}$ is >10 mg/kg p.o. in rats and monkeys.

What is claimed is:

1. A method of preventing or treating chronic rejection in a patient receiving an organ or tissue allo-or xeno-transplant, comprising administering to the patient an effective amount of a compound of formula I or a pharmaceutically acceptable salt thereof:

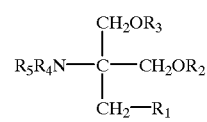

wherein
$R_1$ is an optionally substituted straight or branched carbon chain having 12 to 22 carbon atoms which may be optionally interrupted by an optionally substituted phenylene, and
each of $R_2$, $R_3$, $R_4$ and $R_5$ is independently H or lower alkyl.

2. A method according to claim 1 wherein in the compound of formula I R is phenyl-$C_{1-6}$alkyl wherein the phenyl is substituted by a straight or branched $C_{6-14}$alkyl group, and each of $R_2$, $R_3$, $R_4$ and $R_5$ is H.

3. A method according to claim 2 wherein the compound of formula I is 2-amino-2-[2-(4-octylphenyl)ethyl]-1,3-propanediol or its pharmaceutically acceptable salt.

4. A method according to claim 3 additionally comprising administering to the patient an effective amount of a second immunomodulatory or anti-inflammatory agent.

5. A method according to claim 4 wherein the second immunomodulatory or anti-inflammatory agent is cyclosporin A.

6. A kit or package for preventing or treating manifestations of chronic rejection in a patient receiving an organ or tissue allo- or xeno- transplant comprising an effective amount of a compound of formula I or its pharmaceutically acceptable salt:

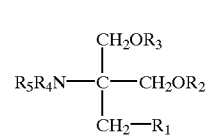

$R_1$ is an optionally substituted straight or branched carbon chain having 12 to 22 carbon atoms which may be optionally interrupted by an optionally substituted phenylene, and
each of $R_2$, $R_3$, $R_4$ and $R_5$ is independently H or lower alkyl,
and an effective amount of a second immunomodulatory or anti-inflammatory agent.

7. A kit or package according to claim 6 wherein in the compound of formula I R is phenyl-$C_{1-6}$alkyl wherein the phenyl is substituted by a straight or branched $C_{6-14}$alkyl group, and each of $R_2$, $R_3$, $R_4$ and $R_5$ is H.

8. A kit or package according to claim 6 wherein the compound of formula I is 2-amino-2-[2-(4octylphenyl)ethyl]-1,3-propanediol or a pharmaceutically acceptable salt thereof.

9. A kit or package according to claim 8 wherein the second immunomodulatory or inflammatory agent is cyclosporin A.

10. A method of preventing or treating chronic rejection in anallograft recipient, comprising administering to the recipient an effective amount of 2-amino-2-[2-(4octylphenyl)ethyl]-1,3-propanediol or its pharmaceutically acceptable salt, optionally with an effective amount of a second immunomodulatory or anti-inflammatory agent.

11. A method of preventing or treating chronic rejection in an allograft recipient, comprising administering to the recipient an effective amount of a compound of formula I or a pharmaceutically acceptable salt thereof:

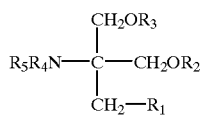

I wherein
  $R_1$ is an optionally substituted straight or branched carbon chain having 12 to 22 carbon atoms which may be optionally interrupted by an optionally substituted phenylene, and
  each of $R_2$, $R_3$, $R_4$ and $R_5$ is independently H or lower alkyl.

12. A method according to claim 11 wherein in the compound of formula I R is phenyl-$C_{1-6}$alkyl wherein the phenyl is substituted by a straight or branched $C_{6-14}$alkyl group, and each of $R_2$, $R_3$, $R_4$ and $R_6$ is H.

13. A method according to claim 11 additionally comprising administering to the patient an effective amount of a second immunomodulatory or anti-inflammatory agent.

14. A method according to claim 12 additionally comprising administering to the patient an effective amount of a second immunomodulatory or anti-inflammatory agent.

15. A method according to claim 13 wherein the second immunomodulatory or anti-inflammatory agent is cydosporin A.

16. A method according to claim 14 wherein the second immunomodulatory or anti-inflammatory agent is cyclosporin A.

17. A method according to claim 14 wherein the compound of formula I is 2-amino-2-[2-(4-octylphenyl)ethyl]-1,3-propanediol or its pharmaceutically acceptable salt and the second immunomodulatory or anti-inflammatory agent is 40-O-(2-hydroxy)ethyl-rapamycin.

18. A method according to claim 14 wherein the compound of formula I is 2-amino-2-[2-(4-octylphenyl)ethyl]-1,3-propanediol or its pharmaceutically acceptable salt and the second immunomodulatory or anti-inflammatory agent is mycophenolic acid or mycophenolate mofetil.

19. A method of preventing or treating chronic rejection in a xenograft recipient, comprising administering to the recipient an effective amount of a compound of formula I or a pharmaceutically acceptable salt thereof:

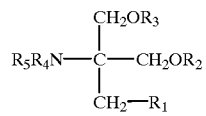

I wherein
  $R_1$ is an optionally substituted straight or branched carbon chain having 12 to 22 carbon atoms which may be optionally interrupted by an optionally substituted phenylene, and
  each of $R_2$, $R_3$, $R_4$ and $R_5$ is independently H or lower alkyl.

20. A method according to claim 19 wherein in the compound of formula I R is phenyl-$C_{1-6}$alkyl wherein the phenyl is substituted by a straight or branched $C_{6-14}$alkyl group, and each of $R_2$, $R_3$, $R_4$ and $R_5$ is H.

21. A method according to claim 20 wherein the compound of formula I is 2-amino-2-[2-(4-octylphenyl)ethyl]-1,3-propanediol or its pharmaceutically acceptable salt.

22. A method according to claim 21 additionally comprising administering to the patient an effective amount of a second immunomodulatory or anti-inflammatory agent.

23. A method according to claim 22 wherein the second immunomodulatory or anti-inflammatory agent is cyclosporin A.

* * * * *

UNITED STATES PATENT AND TRADEMARK OFFICE
CERTIFICATE OF CORRECTION

PATENT NO. : 6,274,629 B1
DATED : August 14, 2001
INVENTOR(S) : Cottens et al.

It is certified that error appears in the above-identified patent and that said Letters Patent is hereby corrected as shown below:

Column 6,
Line 6, should read:
-- A patient receiving an organ or tissue allo- or xeno- --.
Line 62, should read:
-- compound of formula I is 2-amino-2-[2-(4-octylphenyl --.

Column 7,
Line 4, should read:
-- (4-octylphenyl)ethyl]-1,3,-propanediol or its pharmaceutically --.
Line 37, should read:
-- cyclosporin A. --.

Signed and Sealed this

Seventh Day of May, 2002

Attest:

JAMES E. ROGAN
*Attesting Officer*     *Director of the United States Patent and Trademark Office*